(12) United States Patent
Negrello (10) Patent No.: US 12,178,585 B2
(45) Date of Patent: Dec. 31, 2024

(54) MULTI SENSOR AND METHOD (71) Applicant: Enrico Negrello, Riverton, WY (US)

(72) Inventor: Enrico Negrello, Riverton, WY (US)

(73) Assignee: Pertech Industries, Inc., Riverton, WY (US)

(*) Notice: Subject to any disclaimer, the term of this patent is extended or adjusted under 35 U.S.C. 154(b) by 629 days.

(21) Appl. No.: 17/239,024

(22) Filed: Apr. 23, 2021

(65) Prior Publication Data

US 2022/0361798 A1 Nov. 17, 2022

(51) Int. Cl.
A61B 5/346 (2021.01)
A61B 5/00 (2006.01)
A61B 5/145 (2006.01)

(52) U.S. Cl.
CPC .......... A61B 5/346 (2021.01); A61B 5/14542 (2013.01); A61B 5/7246 (2013.01); A61B 5/725 (2013.01); A61B 5/7257 (2013.01)

(58) Field of Classification Search
CPC ... A61B 5/346; A61B 5/14542; A61B 5/7246; A61B 5/725; A61B 5/7257; A61B 5/0245; A61B 5/318; A61B 5/316; A61B 5/1455; A61B 5/14552; A61B 5/14551; A61B 5/7235; A61B 5/7239; A61B 5/7242; A61B 5/7253; A61B 5/726; A61B 5/7271; A61B 5/7275; A61B 5/024; A61B 5/02427; A61B 5/02416
See application file for complete search history.

(56) References Cited

U.S. PATENT DOCUMENTS

| | | | | |
|---|---|---|---|---|
| 5,436,564 | A * | 7/1995 | Kreger | A61B 5/055 324/318 |
| 6,487,295 | B1 * | 11/2002 | Lofgren | H03H 21/0012 381/71.11 |
| 7,174,203 | B2 | 2/2007 | Arand et al. | |
| 9,248,306 | B2 | 2/2016 | Joo et al. | |
| 2004/0143191 | A1 * | 7/2004 | Faisandier | A61B 5/318 600/586 |
| 2011/0319777 | A1 | 12/2011 | Mehrotra et al. | |
| 2015/0065814 | A1 * | 3/2015 | Kapoor | A61B 8/00 600/513 |
| 2017/0209053 | A1 * | 7/2017 | Pantelopoulos | A61B 5/02125 |
| 2017/0319082 | A1 | 11/2017 | Sayme | |
| 2019/0299999 | A1 * | 10/2019 | Liu | G06V 20/597 |

FOREIGN PATENT DOCUMENTS

| | | |
|---|---|---|
| JP | 2012-529951 A | 11/2012 |
| JP | 2016-093488 A | 5/2016 |
| KR | 10-2020-0080755 A | 7/2020 |

OTHER PUBLICATIONS

Springer et al; Logistic regression-hsmm-based heart sound segmentation; IEEE Transactions on Biomedical Engineering; vol. 63, No. Apr. 4, 2016 pp. 822-832.

Schmidt et al.; Segmentation of heart sound recordings by a duration-dependent hidden Markov model; Physiological Measurement 31 (2010) pp. 513-529.

* cited by examiner

Primary Examiner — Paula J Stice (74) Attorney, Agent, or Firm — Reinhart Boerner Van Deuren P.C.

(57) ABSTRACT

A method including the steps of receiving a first signal sensed from a patient, receiving a first physiological signal sensed from the patient, and processing the first signal based at least on the first physiological signal to obtain a second signal that is a measurement of the patient's Heart Rhythm.

8 Claims, 5 Drawing Sheets

MULTI SENSOR AND METHOD

FIELD OF THE INVENTION

This invention generally relates to multi sensors and methods, and more particularly to a method and system for multi-sensor heart rate detection for improved signal accuracy.

BACKGROUND OF THE INVENTION

An electrocardiogram (ECG) is a test that records the electrical activity of the heart thereby measuring Heart Rhythm. The electrical activity is sensed by electrodes attached to the outer surface of the skin. Oximetry Techniques are another means for measuring Heart Rhythm. The recording of the Heart Rhythm using Oximetry Techniques, for example with a multicolored LED and a sensor or an electrocardiogram (ECG) standard multi-lead acquisition system, is usually corrupted by noise from many different sources and can incorporate artifacts from common sources like muscle movements or sensor displacement.

Many existing systems use filtering techniques both hardware, (HW) and software (SW) to obtain a better signal also understood as a wave form of the Heart Rhythm. Thus, signal and wave are interchangeable terms when reference is made herein to Heart Rhythm. The signal/wave is subject to processing to obtain a more accurate signal/wave for diagnosis, especially in the long term analysis, for example where a patient's ECG is recorded continuously for 24 to 48 hours.

The elimination of artifacts, noise, and unnecessary signals has always been a challenge for all the devices currently in use for measuring Heart Rhythm. The presence of these unknown artifacts, noise and signals reduces the confidence in obtaining an accurate ECG signal, that represents a patient's true ECG signal/Heart Rhythm. Further, the presence of these unknown artifacts, noise and signals prevent the use of an automatic algorithm on the sensed ECG signal to obtain the true/accurate ECG signal. This is unfortunate as an accurate heart rhythm from an ECG or Oximeter can be very useful for the detection of pathologies, for example arrhythmias and coronary artery disease.

BRIEF SUMMARY OF THE INVENTION

The invention provides a method and system for improved signal accuracy of a patient's Heart Rhythm. With improved Heart Rhythm signal accuracy clinicians will have a more accurate measurement of a patient's Heart Rhythm and greater confidence in accurately diagnosing heart related pathologies in their patients. These and other advantages of the invention, as well as additional inventive features, will be apparent from the description of the invention provided herein.

The invention provides for the use of both hardware and software and a method therefore in order to enhance the quality of the signals received from multiple sensors being used to measure the Heart Rhythm. The method and system disclosed by the invention uses a first sensor for measuring the Heart Rhythm, for example the electrodes of an ECG device which produce an ECG signal or an Oximetry based sensor. A second sensor, namely a physiological sensor is chosen based on its known correlation with Heart Rhythm. By physiological sensor it is meant that the sensor measures a physiological parameter of the body, for example, the sound of the beating heart, the body's thoracic impedance, the electrical activity of the heart, oxygen saturation levels in the blood (e.g. oximeters).

These physiological measurements are known to have a direct correlation to Heart Rhythm. The physiological sensor may be, but is not limited to, a microphone that might be typically used in phonocardiogram (PCG) or the electrodes associated with producing a signal that measures thoracic impedance, or the sensors of an oximeter record the light transmitted through the blood to measure oxygen saturation which in turn correlates directly with Heart Rhythm. Selection of the second senor is therefor based on whether there is correlation between the two signals measured by the sensors. For example, it is known that there is a correlation between a patient's measured ECG signal and the patient's measured PCG signal. In other words, if one knows the ECG signal measuring Heart Rhythm then it can be used to estimate the likely PCG signal for the Heart Rhythm and vice versa.

In contrast, to correlated signals there are sensors which while providing useful information for determining Heart Rhythm, have no correlation with the actual measured Heart Rhythm of a patient. For example, a gyroscope might be used at the same time an ECG is used. The gyroscope records the orientation of a patient during an ECG. The sensed orientation translates as noise in the signal recorded by the ECG. Therefore, the gyroscopes readings can be subtracted from the recorded ECG signal, by known means familiar to those skilled in the art, for example through adaptive filters, to produce a more accurate ECG signal. However, there is no correlation between the patient's orientation as recorded by the gyroscope and Heart Rhythm. Therefore, while embodiments of this invention may use such noise measuring sensors, they are used in conjunction with the two sensed physiological signals to produce an accurate ECG signal that best represents the patient's true Heart Rhythm.

A hardware and software method for enhancing the quality of the signals from a multi sensor device aimed to measure the Heart Rhythm using classic ECG signals and Oximetry based sensors is provided. Based on the correlation between the ECG signal and other signals, like for example, the sound signal from a microphone applied to the chest, a method is provided to cross-correlate the signals and to adaptively filter them. The method is not only using the cross-correlation between signals to improve the quality of them, by removing artifacts and undesired noise, but it is also defining a method to automatically score the quality of the signals. For example, undesired artifacts are generated by displacement of patches on the body; by correlating the movement of the body using an accelerometer sensor these artifacts can be identified. The quality score of the signal can be used on a long term automated analysis.

In an embodiment of the present method, a three lead ECG and a microphone PCG incorporated with an accelerometer sensor and gyroscope sensor are correlated by means of an adaptive and recursive filter to clean up each of the signals waveforms from the two sensors, namely the ECG and PCG.

The method uses a different signal, that is a second signal that is not the ECG signal, to filter as the input data for an adaptive filter algorithm to obtain a more accurate ECG signal indicative of the patient's true Heart Rhythm.

In one aspect, the invention provides a method. The method includes the steps of receiving a first signal sensed from a patient, receiving a first physiological signal sensed from the patient, and processing the first signal based at least on the first physiological signal to obtain a second signal that is a measurement of the patient's Heart Rhythm.

In an embodiment, the step of receiving the first signal includes the step of receiving an electrocardiogram signal or an oximeter signal.

In an embodiment the method includes the step of selecting the first physiological signal based upon its correlation with first signal.

In an embodiment, the step of processing the first signal includes the step of applying a first adaptive filter to the first signal.

In an embodiment, the method includes the step of processing the first physiological signal to obtain a desired first signal.

In an embodiment, the step of processing the first physiological signal includes the step of applying a first transformation algorithm to the first physiological signal to obtain the desired first signal.

In an embodiment, the step of processing the first physiological signal includes the step of applying a second adaptive filter to the first physiological signal followed by the first transformation algorithm to the first physiological signal to obtain the desired first signal.

In an embodiment, the method includes the step of inputting the desired first signal into the first adaptive filter to obtain the second signal.

In an embodiment, the step of processing the first physiological signal to obtain the desired first signal includes the step of preprocessing a second raw signal to obtain the first physiological signal. The preprocessing of the second raw signal includes the steps of amplifying the signal, applying a low band filter to the signal, converting the signal from an analog signal to a digital signal, sampling the digital signal, applying a Fast Fourier Transform to the digital signal and outputting the first physiological signal.

In an embodiment, the method includes the step of processing the first physiological signal based at least on the first signal to obtain a second physiological signal.

In an embodiment, the method includes the steps of applying a second adaptive filter to the first physiological signal to obtain the second physiological signal.

In an embodiment, the method includes the steps of applying a second transformation algorithm to the second signal to obtain a desired physiological signal.

In an embodiment, the method includes the step inputting the desired physiological signal into the second adaptive filter to obtain the second physiological signal.

In an embodiment, the step of receiving the first physiological signal includes the step of receiving the first physiological signal from a microphone.

In an embodiment, the method includes the steps of receiving a third raw signal that is not a signal that correlates to either the first signal or the first physiological signal, and inputting the second raw signal into the first adaptive filter to obtain the second signal.

In another aspect the invention provides a system. The system includes a first sensor for measuring a first signal sensed from a patient. The system includes a physiological sensor for measuring a physiological parameter of the patient that correlates with the first signal. The system includes a processor programed to process the first signal based at least on the first physiological signal to obtain a second signal that is a measurement of the patient's Heart Rhythm.

In an embodiment the processor applies a second adaptive filter and a first transformation algorithm to the first physiological signal to determine a desired first signal.

In an embodiment, the desired first signal is an input into a first adaptive filter applied by the processor to derive the second signal.

In an embodiment, the processor applies a first adaptive filter and a second transformation algorithm to the first signal to obtain a desired physiological signal.

In an embodiment, the desired physiological signal is an input into a second adaptive filter applied by the processor to derive the second physiological signal.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
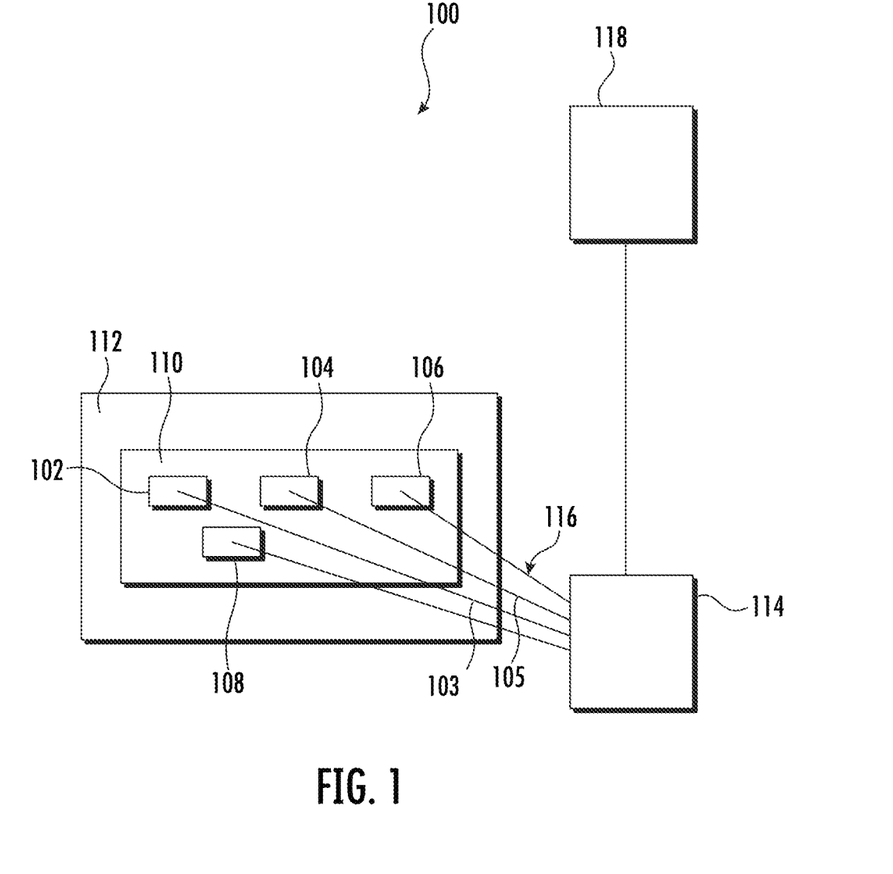
FIG. 1 is a schematic illustration of a system according to the teachings of the instant application.

Turning now to the drawings, there is illustrated in FIG. 1 an exemplary embodiment of a system 100 for Heart Rhythm detection with improved signal accuracy. The system 100 includes multi sensors 102, 104, 106, and 108 but may have as few as two sensors 106 and 108, but may include more than the four sensors shown. Indeed an embodiment may include as sensors, electrodes, a gyroscope, an accelerometer a magnetometer and temperature sensor.

The system 100 includes an apparatus 110 that may be placed on, carried by, or worn by a patient 112. The apparatus 110 may be for example, a belt, harness, vest, or clips, by way of non-limiting examples. In an embodiment, not illustrated, there may not be an apparatus 110 that holds the sensors 102, 104, 106, 108, but instead, for example in a bed ridden patient who is fairly sedentary, the sensors 102, 104, 106, 108, may be directly attached to the patient 112 without the need for apparatus 110.

The sensors 102, 104, 106, 108, may include, for example, a first sensor 102 that is an electrode or pair of electrodes for sensing then electrical activity of the patient's 110 heart and transmitting that electrical activity as a first raw signal 103. It is not the intent to limit the first sensor 102 to an electrode. Other examples may provide for the first sensor 102 that is an oximeter. Another of the sensors 102, 104, 106, 108, may be a physiological sensor 104 that is a microphone for measuring the sound of the patient's 112 heart and transmitting the sound as a second raw signal 105.

Alternatively, the second sensor 104 could be another electrode for measuring thoracic impedance. Another of the sensors 102, 104, 106, 108 may be an accelerometer or gyroscope that may sense the patient's movement. Sensors such as accelerometers or gyroscopes are understood by those in the art to measure "noise" while the Heart Rhythm is being measured. Thus, the measurements by an accelerometer or gyroscope are considered signals that interfere, that is create noise, and mask the true sensed signals representing the patient's 112 Heart Rhythm. This noise may be accounted for in the method, for example as will be discussed with respect to FIG. 5 for the operating the system 100.

The system 100 further includes a processor 114, which may be for example in a personal computer (PC) or local server or cloud based server or mobile device by way of non-limiting examples. The processor 114 is equipped with a memory and able to execute programs for processing signals 116 received of the sensors 102, 104, 106, 108, via wire connections or other known communication means such as wireless transmission. The processing signals 116 may be, for example the first raw signal 103 or the second raw signal 105.

The processor 114 is able to store and permit retrieval by a user of the signals 116 and the signals 116 that have been processed by the processor 114. The user may be, for example, a medical professional such as a cardiologist interested in the patient's 112 Heart Rhythm for diagnosing pathologies related to the heart. The system 100 also includes a display 118 for viewing by the user the signals 116 that have processed.

Figure 2:
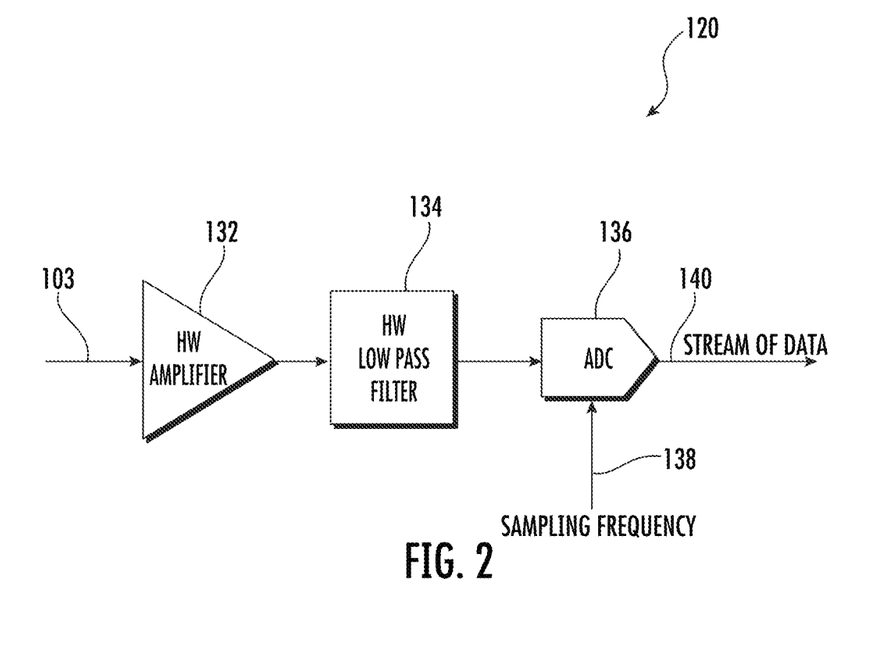
FIG. 2 illustrates steps of a method applied to a first raw signal according to the teachings of the instant application.

FIG. 2 illustrates the preprocessing steps of a method 120 according to the teachings of the instant application. The first raw signal 103 is measured by the first sensor 102 (FIG. 1). The first sensor 102 (FIG. 1) may be an electrode or pair of electrodes that sense the heart's electrical activity and produces the first raw signal 103 that is a voltage processed to output a second signal 124 (FIG. 5) that is a measurement of a patient's Heart Rhythm. Thus, the second signal 124, may be, for example, an ECG signal 126 (FIG. 3) that is typically displayed to the physician as the patient's measured Heart Rhythm in amplitude over time.

Figure 3:
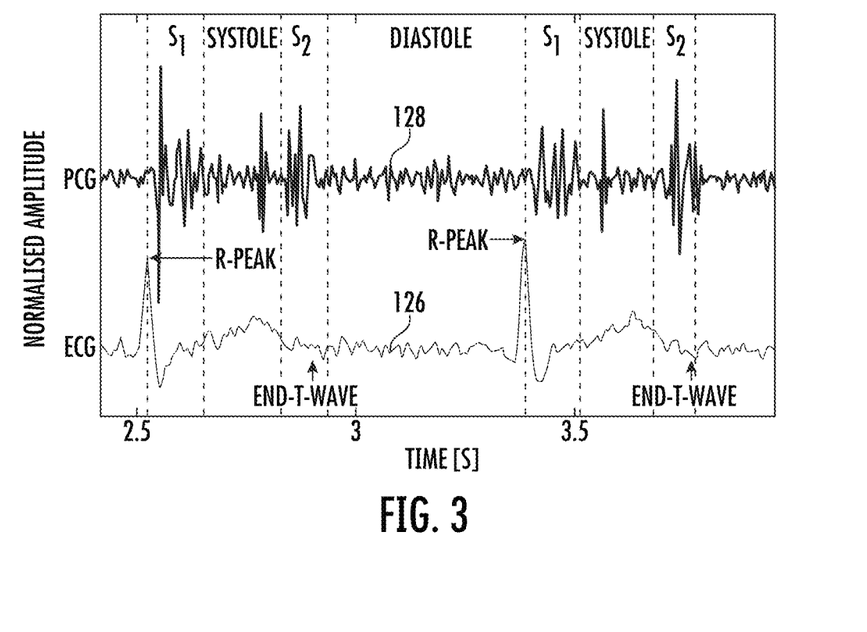
FIG. 3 illustrates a correlation between two sensed signals of a patient, namely an ECG signal and a PCG signal.

One of the objectives of the instant invention's system and method is to produce a more accurate measurement of a patient's Heart Rhythm, that is, the second signal 124 visualized as an ECG signal 126 (FIG. 3) and the second physiological signal 128 visualized as the PCG signal 130 (FIG. 3) than has been heretofore known. Accordingly, the method 120 discussed with respect to FIGS. 1-5 refers to the first raw signal 103 sensed by electrodes 102 (FIG. 1) used to produce the second signal 124 (FIG. 4) and the second raw signal 105 (FIG. 1) sensed by the second sensor 104 (FIG. 1) that is a microphone used to produce the second physiological signal 128 (FIG. 4) visualized as a PCG signal 130 (FIG. 3). While such an exemplary embodiment will be utilized in describing various features and advantages of embodiments of the invention, such a description should be taken by way of example and not by limitation.

Still with respect to FIG. 2, the method 120 provides for the preprocessing, also referred to as filtering, of the first raw signal 103, sensed by the first sensor 102 (FIG. 1) that is an electrode or pair of electrodes. The first raw signal 103 is amplified at step 132 and is then passed through an HW Low Pass Filter at step 134. Thereafter, the raw signal 103 is converted to a digital signal at step 136. The digital signal is a data flow that is sampled at step 138. The sample rate as Fs supposes that the HW amplification of the raw signal 103 and pre-filtering has already filtered the signal for low pass, eliminating all the frequencies higher than Fs/2 of the sample rate to avoid undesired artifacts. This results in a stream of data (Xk) where X is a number representing the value of a first signal 140 at the k instant.

More specifically with respect to the preprocessing, the raw signal 103 is sampled at 1 KHz. The HW low pass filter at step 134 is applied to filter frequencies higher than 400 Hz and then another low pass FIR filter is applied to the digitized signal. A simple spike removal algorithm is also applied. A parabolic regression of consecutive 16 points and the corresponding standard deviation index number is performed with the points that exceed the predetermined threshold eliminated.

Prior to any other event, the exact location of the main components amongst the heart sound events which are S1 and S2 and ECG wave components R-Peak and T-wave are detected. In order to do the accurate segmentation of these signals in noisy real-world datasets from normal and abnormal heart recordings, an automatic segmentation algorithm is used. Because the spikes have been removed and a band pass FIR filter applied a modified Pan-Tompkins algorithm is used to detect the QRS complex. Then the QRS peak is compared to the S1 sound power and spectrum to eliminate false T waves confused for R peak as discussed in Springer D B, Tarassenko L, Clifford G D. Logistic regression-hsmm-based heart sound segmentation. IEEE Transactions on Biomedical Engineering 2016; 63(4):822— 832, the entire teachings of which are incorporated herein by reference thereto.

FIG. 3 illustrates the correlation between the measured sound of the heart as expressed by the PCG signal 128 and the measured electrical activity of the heart as expressed by the ECG signal 126. In this sense both the ECG signal 126 and the PCG signal 128 are both derived from physiological sensed parameters that have a direct correlation to one another. Normal heart sounds are associated with heart valves closing and blood flow. The correlation of heart sound and ECG signal 126 (FIG. 3) is then achieved by analyzing the second raw signal 105 which is a sound signal in magnitude and frequency. In healthy adults, there are two normal heart sounds, often described as a lub and a dub, that occur in sequence with each heartbeat. These are the first heart sound (S1) and second heart sound (S2), produced by the closing of the atrioventricular valves and semilunar valves, respectively.

The electrical activity that triggers the contraction and relaxation of the heart and hence the opening and closing of its valves has a measurable correlation between the sounds made by the contracting and relaxing heart, that is the opening and closing of its valves. However, as previously discussed, not every sensed parameter that is measured during an ECG or PCG is physiological nor in some cases, even where it may be physiological, the sensed physiological parameter may not have a correlation with the patient's Heart Rhythm. However, embodiments of the method of this invention require at least a first sensor 103 (FIG. 1) and a second sensor (FIG. 1) that have a correlation between the first raw signal 103 (FIG. 1) and the second raw signal 105 (FIG. 1).

Figure 4:
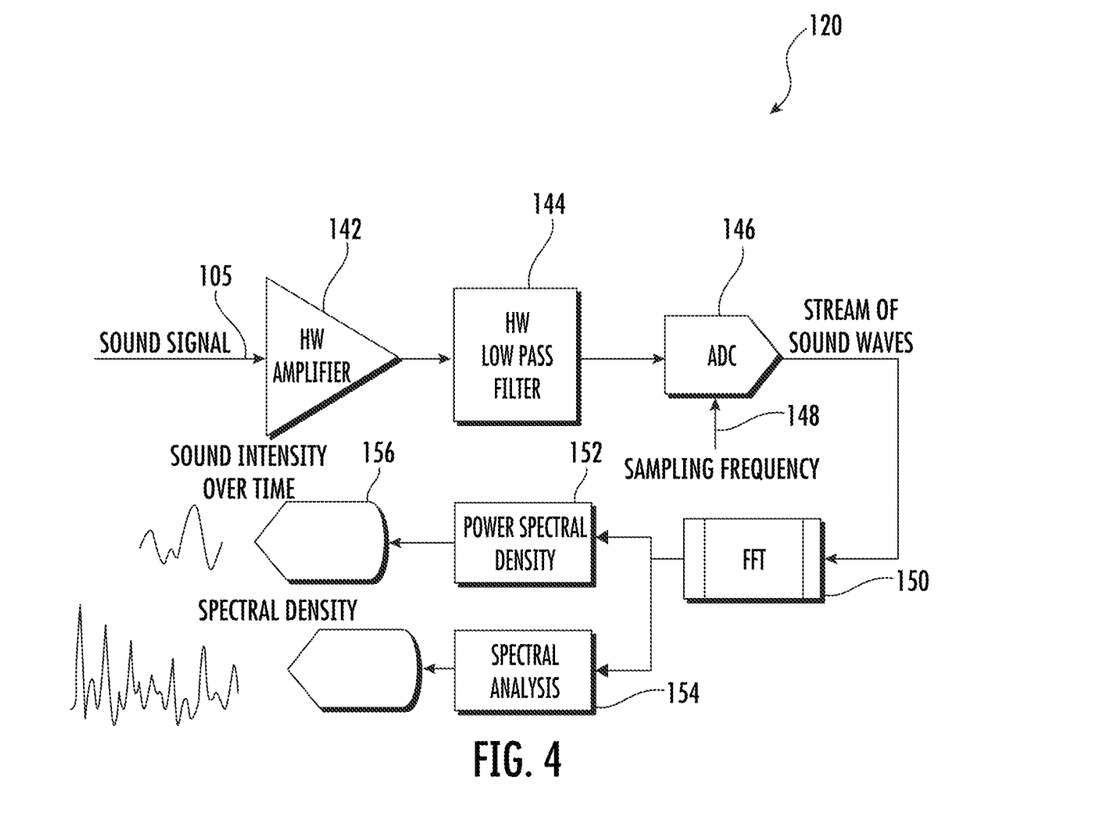
FIG. 4 illustrates further steps of the method applied to a second raw signal.

Turning now to FIG. 4, a preprocessing of the second raw signal 105 according to the method 120 is illustrated. The second raw signal 105 is sensed at the same time the first raw signal 103 (FIG. 1) is sensed and therefore, there is a simultaneous processing including preprocessing of the first raw signal 103 (FIG. 2) and the second raw signal 105. As discussed previously the second raw signal 105 is sensed by a microphone sensing the sounds of the heart. The second raw signal 105, which in the illustrated example is the sensed sound from a microphone on a patient, is amplified at step 142.

After the second raw signal is amplified, it is passed through a HW Low Pass Filter at step 144. Thereafter, the second raw signal 105 (FIG. 1) is converted to a digital signal at step 146. The digital signal is a data flow that is sampled at step 148. This results in a stream of data that is subject to a Fast Fourier Transform (FFT) at step 150. The FFT algorithm is applied to the digital signal to obtain a frequency behavior of the sound over time, and in particular between systole and diastole rhythm as seen in FIG. 3. As a result of the application of the preliminary FFT algorithm a power spectral density 152 and a spectral analysis 154 are obtained. The power spectral density is a sound intensity signal referred to as a first physiological signal 156.

More specifically with respect to the preprocessing steps of the second raw signal 105 (FIG. 1) that is a sound signal, the second raw signal 105 (FIG. 1) is sampled at 2 kHz. Because the possible frequency range for cardiac sounds is between 25 and 400 Hz, the band pass filter with cut-off frequencies at 25 Hz and 400 Hz is applied to the second raw signal 105 (FIG. 1). The removal of spikes which are sometimes higher in amplitude than the heart sounds is performed using an algorithm that correlates the expected sound from an acquired ECG signal that will be discussed in greater detail below. The signal is then normalized to map the amplitudes to a reference line.

As was discussed with respect to the first raw signal 103 (FIG. 1), for the second raw signal 105 (FIG. 1) the exact location of the main components amongst the heart sound events which are S1 and S2 and ECG wave components R-Peak and T-wave are detected. An automatic segmentation algorithm is used. More specifically, at step 150 the FFT algorithm is used to obtain the mean amplitude spectrum of the systolic and diastolic regions.

The FFT is performed on a sample of 512 points which at 4 Khz sampling rate is 125 mS, the systolic interval varies approximately between 170 mS for a 160 bpm to 550 mS for 30 bpm. The starting point for the search of the S1, S2 segment is acquired from the ECG signal and compared to the expected normal sound, the comparison is done with a convolution algorithm. Such algorithms are discussed for example in, Schmidt S E, Holst-Hansen C, Graff C, Toft E, Struijk J J. Segmentation of heart sound recordings by a duration-dependent hidden Markov model. Physiological Measurement 2010; 31(4):513, the entire teachings of which are incorporated herein by reference thereto.

Figure 5:
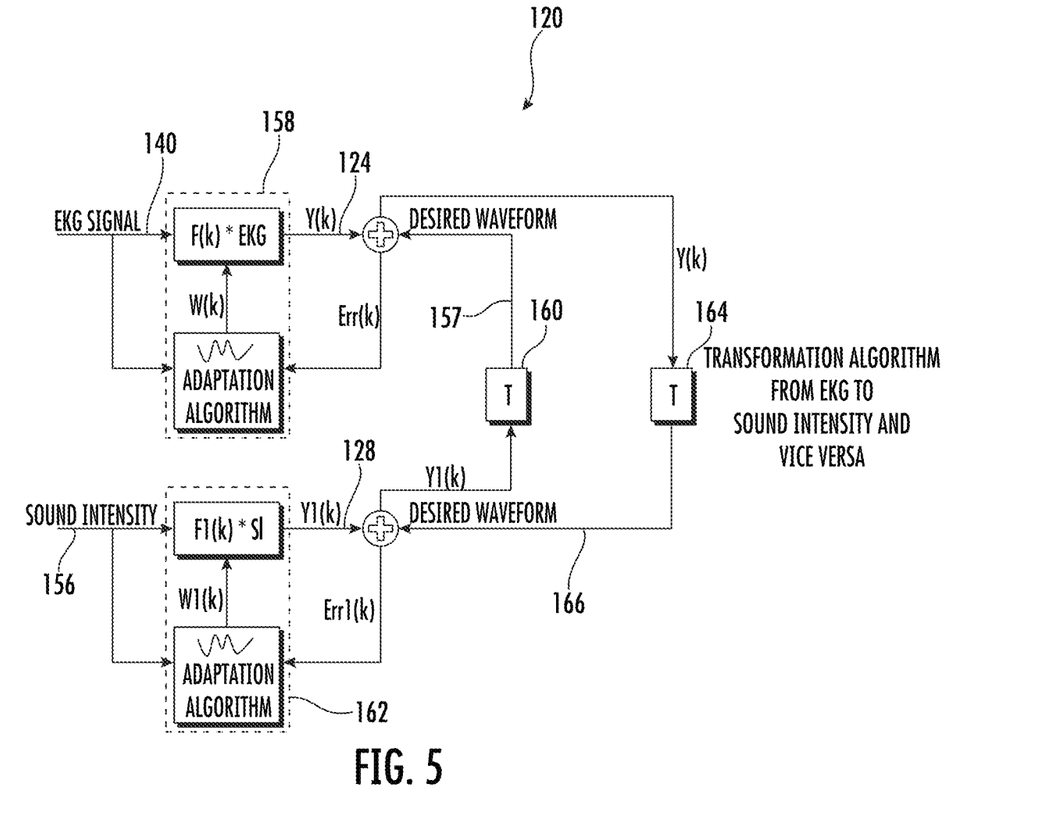
FIG. 5 illustrates further steps of the method applied to both the first raw signal and the second raw signal.

FIG. 5 illustrates the final processing steps of the method 120. At step 158 a first adaptive filter is applied to the first signal 140. The first adaptive filter may use the first physiological signal 156 that has been subject to a first transformation algorithm at step 160 to obtain a desired first signal 157 that is then input into the first adaptive filter at step 158 to obtain the second signal 124. Preferably, however, for greater accuracy in deriving the second signal 124, a second adaptive filter at step 162 is applied to the first physiological signal 156 to obtain the second physiological signal 128. Thereafter, the first physiological signal 128 is input into the first transformation algorithm at step 160 to obtain the desired first signal 157 which is then the input into the first adaptive filter at step 158 to obtain the second signal 124.

The method just described with respect to FIG. 4 to derive the second signal 124 that is the ECG signal 126 displayed at FIG. 3 is also used to determine the second physiological signal 128 that is the PCG signal 128 displayed at FIG. 3. More specifically, at step 162 the second signal 124 is subject to a second transformation algorithm at step 164 to derive a desired physiological signal 166 that is then input into the second adaptive filter at step 162 to derive the second physiological signal 128.

Still with respect to FIG. 5, the first transformation algorithm 160 and the second transformation algorithm 164 are applied to both signals from the ECG to the PCG and from the PCG to the ECG as was explained above. With the segmented waveform of the ECG an expected wave for the PCG and the ECG are derived, namely the desired physiological signal 166 and the desired first signal 157. The first transformation algorithm 160 and the second transformation algorithm 164 accumulate previous signals of each ECG and PCG and generate a "sample waveform" or mean waveform, these 2 waveforms are used as the samples to be linked in time and amplitude. Characteristic parameters are generated from the segmentation of the signal and specific links are extracted.

Still with respect to FIG. 5, adaptive filtering on ECG signals has been used extensively but heretofore it has been difficult to define the parameters of a filter that are not known "a priori" because they are changing. By using the second raw signal 105 (FIG. 1) from the second senor 104 (FIG. 1) and by way of specific example, a microphone, to define these parameters for the first adaptive filter 158, the uncertainty of having used an inaccurate parameter is eliminated. The assumption on this methodology is that the two signals, namely the first raw signal 103 (FIG. 1) and the second raw signal 105 (FIG. 1) have a correlation but the noise that should be filtered does not. Regarding the first and second adaptive filters 158 and 162, the following describes the algorithms:

$$Y(n) = \sum_{k=0}^{k=N-1} W_k(n) * X(n-k)$$

Where W(k) are obtained by a recursive algorithm that minimize the quadratic error between the desired waveform and the obtained filtered waveform. Because it can be inferred that X(n) are a mix of good signal and noise it can be express X(n)=G(n)+N(n) and then express Y(n) as:

$$Y(n) = \sum_{k=0}^{k=N-1} W_k(n) * G(n-k) + \sum_{k=0}^{k=N-1} W_k(n) * N(n-k)$$

Therefore, $\sum_{k=0}^{k=N-1} W_k(n) * G(n-k)$ can be substituted with the desired waveform D(n) obtained from the other correlated signal. The equation is then solved as a bi-dimensional Matrix using Cramer's rule.

During real time acquisition the W(k) are constantly modified by the desired waveform calculation from the transformation algorithms. The expected waveform could be different from the acquired, so it is necessary to reapply the adaptive filtering in order to re-generate the expected waveform in a loop that minimizes the quadratic error (the convolution of the 2 waveforms).

The ability of reaching a minimum (convergence) is determined by the amount of noise and the ratio between signal and noise. Artifacts like movement of the electrodes and extra sound in the ambient are removed quite well if the signal is strong enough.

Figure 6:
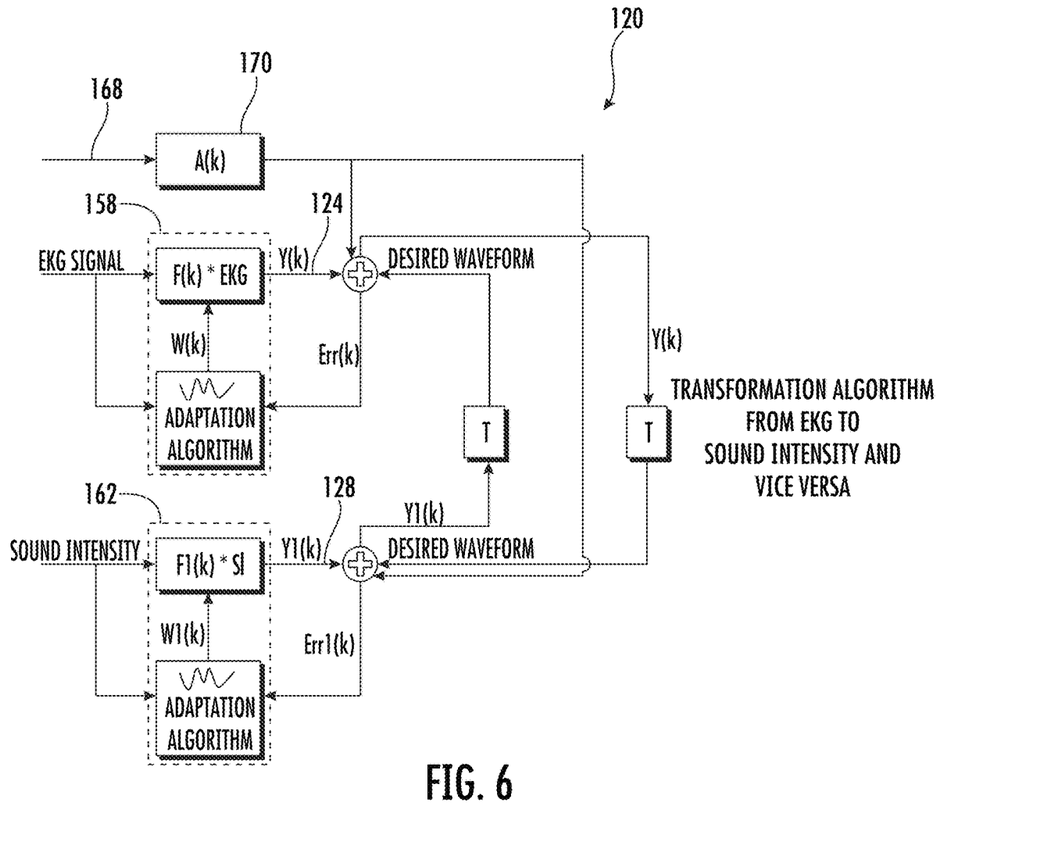
FIG. 6 illustrates further steps of the method applied to a third raw signal having no correlation to the first and the second raw signals.

FIG. 6 illustrates further steps that may be used in the method 120 where a third sensor 106 (FIG. 1) is used for sensing undesired noise and that does not have any correlation with the first raw signal 103 (FIG. 1) nor the second raw signal 105 (FIG. 1). In this example, the third sensor 106 (FIG. 1) is an magnetometer that senses the third raw signal 168. The magnetometer is not a physiological parameter that correlates to a patient's Heart Rhythm but instead is useful in measuring the noise that the patient makes during the patient's movement. The third raw signal 168 may be subject to filtering at step 170 and then may be an into either or both the first adaptive filter at step 158 or the second adaptive filter at step 162 to subtract out the noise to derive the second signal 124 or the second physiological signal 128.

It is not the intent to limit the third raw signal 168 to that produced by a magnetometer. For example, other noise can be sensed and subtracted out, for example the frequency of the electrical power/generator that powers the system 100 (FIG. 1). Further, more than one sensed noise could be provided for in the method 120. In other words, for example, generator noise just discussed could be an input into the first and the second adaptive filters 158, 162 together with the input from the magnetometer. Thus, while the method provides for two correlated sense signals 124, 128, other sensors may be utilized that may either be correlative to heart rhythm or may be noise that can be subtracted as just described.

Embodiments of the invention are further disclosed below.

Embodiment 1: a method comprising: receiving a first signal sensed from a patient; receiving a first physiological signal sensed from the patient; and processing the first signal based at least on the first physiological signal to obtain a second signal that is a measurement of the patient's Heart Rhythm.

Embodiment 2: An embodiment according to embodiment 1, wherein the step of receiving the first signal includes the step of receiving an electrocardiogram signal or an oximeter signal.

Embodiment 3: An embodiment according to any one of the embodiments 1-2, including the step of selecting the first physiological signal based upon its correlation with first signal.

Embodiment 4: An embodiment according to any one of the embodiments 1-3, wherein the step of processing the first signal includes the step of applying a first adaptive filter to the first signal.

Embodiment 5: An embodiment according to any one of the embodiments 1-4 including the step of processing the first physiological signal to obtain a desired first signal.

Embodiment 6: An embodiment according to embodiment 5, wherein the step of processing the first physiological signal includes the step of applying a first transformation algorithm to the first physiological signal to obtain the desired first signal.

Embodiment 7: An embodiment according to claim 5, wherein the step of processing the first physiological signal includes the step of applying a second adaptive filter to the first physiological signal followed by the first transformation algorithm to the first physiological signal to obtain the desired first signal.

Embodiment 8: An embodiment according to embodiment 6 or embodiment 7, including the step of inputting the desired first signal into the first adaptive filter to obtain the second signal.

Embodiment 9: An embodiment according to any one of embodiments 1-8, wherein the step of processing the first physiological signal to obtain the desired first signal includes the step of preprocessing a second raw signal to obtain the first physiological signal, the preprocessing of the second raw signal comprising the steps of: amplifying the signal; applying a low band filter to the signal; converting the signal from an analog signal to a digital signal; sampling the digital signal; applying a Fast Fourier Transform to the digital signal; outputting the first physiological signal.

Embodiment 10: An embodiment according to any one of the previous embodiments 1-9 including the step of processing the first physiological signal based at least on the first signal to obtain a second physiological signal.

Embodiment 11: An embodiment according to embodiment 10 including the step of applying a second adaptive filter to the first physiological signal to obtain the second physiological signal.

Embodiment 12: An embodiment according any one of the embodiments 1-11, including the step of applying a second transformation algorithm to the second signal to obtain a desired physiological signal.

Embodiment 13: An embodiment according to embodiment 12, including the step of inputting the desired physiological signal into the second adaptive filter to obtain the second physiological signal.

Embodiment 14: An embodiment according to any one of the embodiments 1-13, wherein the step of receiving the first physiological signal includes the step of receiving the first physiological signal from a microphone.

Embodiment 15: An embodiment according to any one of the embodiments 1-14 including the steps of receiving a third raw signal that is not a signal that correlates to either the first signal or the first physiological signal; and inputting the second raw signal into the first adaptive filter to obtain the second signal.

Embodiment 16: A system comprising: a first sensor for measuring a first signal sensed from a patient; a physiological sensor for measuring a physiological parameter of the patient and that correlates with the first signal; a processor programed to process the first signal based at least on the first physiological signal to obtain a second signal that is a measurement of the patient's Heart Rhythm.

Embodiment 17: An embodiment according to embodiment 16, wherein the processor applies a second adaptive filter and a first transformation algorithm to the first physiological signal to determine a desired first signal.

Embodiment 18: An embodiment according to embodiment 17, wherein the desired first signal is an input into a first adaptive filter applied by the processor to derive the second signal.

Embodiment 19: An embodiment according to any one of embodiments 16-18, wherein the processor applies a first adaptive filter and a second transformation algorithm to the first signal to obtain a desired physiological signal.

Embodiment 20: An embodiment according to embodiment 19, wherein the desired physiological signal is an input into a second adaptive filter applied by the processor to derive the second physiological signal.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of measurement of a patient's heart rhythm as a voltage verses time, comprising:
    positioning an apparatus on a patient proximate a chest of the patient, the apparatus comprising a first sensor that is an electrode or an oximeter, and a second sensor being a phonocardiogram microphone;
    first sensing a first raw signal from the patient using the first sensor;
    preprocessing the first raw signal, the preprocessing including the steps of:
        amplifying the first raw signal;
        applying a low band filter to the first raw signal;
        converting the first raw signal from a first analog signal to a first digital signal;
        sampling the first digital signal to obtain a first signal;
    second sensing a second raw signal from the patient using the second sensor, the first sensing and the second sensing being at the same time;
    preprocessing the second raw signal, the preprocessing including the steps of:
        amplifying the second raw signal;
        applying another low band filter to the second raw signal;
        converting the second raw signal from a second raw analog signal to a second raw digital signal;
        sampling the second raw digital signal;
        applying a Fast Fourier Transform to the samples of the second raw digital signal to determine a frequency behavior over time as a first physiological signal;
    transmitting the first signal and the first physiological signal to a processor;
    storing the first signal and the first physiological signal in a memory of the processor;
    processing, using the processor, the first signal based at least on the first physiological signal to obtain a second signal that is a measurement of the patient's heart rhythm;
        wherein the processing comprises:
            applying a second adaptive filter to the first physiological signal followed by a first transformation algorithm to obtain a desired first signal;
            inputting the desired first signal into a first adaptive filter;
            inputting the first signal into the first adaptive filter;
            applying the first adaptive filter to the first signal and the first desired signal to determine the second signal that is the patient's heart rhythm,
    storing the measurement of the patient's heart rhythm in the memory;
    displaying on a mobile device the measurement of the patient's heart rhythm.

2. The method of claim 1, wherein the first raw signal sensed by the electrode is an electrocardiogram signal.

3. The method of claim 1, wherein there is a correlation between the first raw signal and the second raw signal.

4. The method of claim 1, wherein the apparatus comprises:
    a third sensor sensing a third raw signal from movement of the patient;
    wherein the third raw signal is not a signal that correlates to either the first signal or the first physiological signal; and
    filtering the third raw signal and inputting the filtered third raw signal into the first adaptive filter to obtain the second signal.

5. The method of claim 4, wherein the third sensor is an accelerometer.

6. A system for measurement of a patient's heart rhythm as voltage versus time to diagnose heart related pathologies comprising:
    the apparatus, the first sensor, the second sensor, the processor and memory and mobile device of claim 1,
    the processor and memory configured to carry out the method of claim 1;
    the mobile device including the processor and the memory; the mobile device including a display for displaying the measurement of the patient's heart rhythm.

7. The system of claim 6, wherein the apparatus comprises a third sensor configured to sense a third raw signal from movement of the patient;
    wherein the third raw signal is not a signal that correlates to either the first signal or the first physiological signal; and wherein the processor is configured to input the third raw signal into the adaptive filter to obtain the second signal.

8. The method of claim 1, wherein the first signal is an oximeter signal.

* * * * *

UNITED STATES PATENT AND TRADEMARK OFFICE
CERTIFICATE OF CORRECTION

PATENT NO. : 12,178,585 B2
APPLICATION NO. : 17/239024
DATED : December 31, 2024
INVENTOR(S) : Enrico Negrello

Page 1 of 1

It is certified that error appears in the above-identified patent and that said Letters Patent is hereby corrected as shown below:

In the Claims

Column 11, Claim 1, Line 2 reads: "as a voltage verses time, comprising:"
Should read: --as a voltage versus time, comprising:--

Signed and Sealed this
Eighteenth Day of February, 2025

Coke Morgan Stewart
*Acting Director of the United States Patent and Trademark Office*